(12) United States Patent
Yamanaka et al.

(10) Patent No.: US 10,238,290 B2
(45) Date of Patent: Mar. 26, 2019

(54) PROBE FOR BIOINSTRUMENTATION AND BIOINSTRUMENTATION DEVICE

(71) Applicant: HAMAMATSU PHOTONICS K.K., Hamamatsu-shi, Shizuoka (JP)

(72) Inventors: Takahiko Yamanaka, Hamamatsu (JP); Shigeo Hara, Hamamatsu (JP); Toru Hirohata, Hamamatsu (JP); Takashi Watanabe, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 718 days.

(21) Appl. No.: 14/666,482

(22) Filed: Mar. 24, 2015

(65) Prior Publication Data
US 2015/0276206 A1    Oct. 1, 2015

(30) Foreign Application Priority Data

Mar. 27, 2014  (JP) ................. 2014-065645

(51) Int. Cl.
*A61B 5/1455*   (2006.01)
*A61B 5/00*   (2006.01)

(52) U.S. Cl.
CPC .......... *A61B 5/0059* (2013.01); *A61B 5/1455* (2013.01); *A61B 2560/0412* (2013.01); *A61B 2562/0238* (2013.01); *A61B 2562/164* (2013.01); *A61B 2562/222* (2013.01)

(58) Field of Classification Search
CPC . A61B 5/0059; A61B 5/1455; A61B 5/14551; A61B 5/14552; A61B 5/14532; A61B 2562/00; A61B 2562/02; A61B 2562/0233; A61B 2562/0238; A61B 2562/16; A61B 2562/164; A61B 2562/166; A61B 2562/185
See application file for complete search history.

(56) References Cited

U.S. PATENT DOCUMENTS

| | | | | |
|---|---|---|---|---|
| 5,797,841 | A * | 8/1998 | Delonzor | A61B 5/14552 250/221 |
| 6,483,099 | B1 * | 11/2002 | Yu | B82Y 10/00 250/214.1 |
| 6,801,799 | B2 * | 10/2004 | Mendelson | A61B 5/14552 600/322 |
| 2007/0129613 | A1 * | 6/2007 | Rochester | A61B 5/14546 600/310 |
| 2009/0054752 | A1 | 2/2009 | Jonnalagadda et al. | |
| 2012/0136227 | A1 * | 5/2012 | McKenna | A61B 5/14551 600/324 |

FOREIGN PATENT DOCUMENTS

| | | |
|---|---|---|
| JP | 2001-094089 | 4/2001 |
| JP | 2008-103670 A | 5/2008 |
| JP | 2009-003821 | 1/2009 |
| JP | 2009-231577 | 10/2009 |
| JP | 2013-000158 | 1/2013 |
| JP | 2013-009710 | 1/2013 |

* cited by examiner

*Primary Examiner* — Eric Winakur
*Assistant Examiner* — Chu Chuan (JJ) Liu
(74) *Attorney, Agent, or Firm* — Drinker Biddle & Reath LLP

(57) ABSTRACT

With a probe 2 in which an end of the organic photoelectric-conversion layer 23 on a projection optical path 10 side is covered by an upper electrode 24 having a light-blocking effect, light passing through the projection optical path 10 from a light source can be prevented from directly entering the organic photoelectric-conversion layer 23.

6 Claims, 9 Drawing Sheets

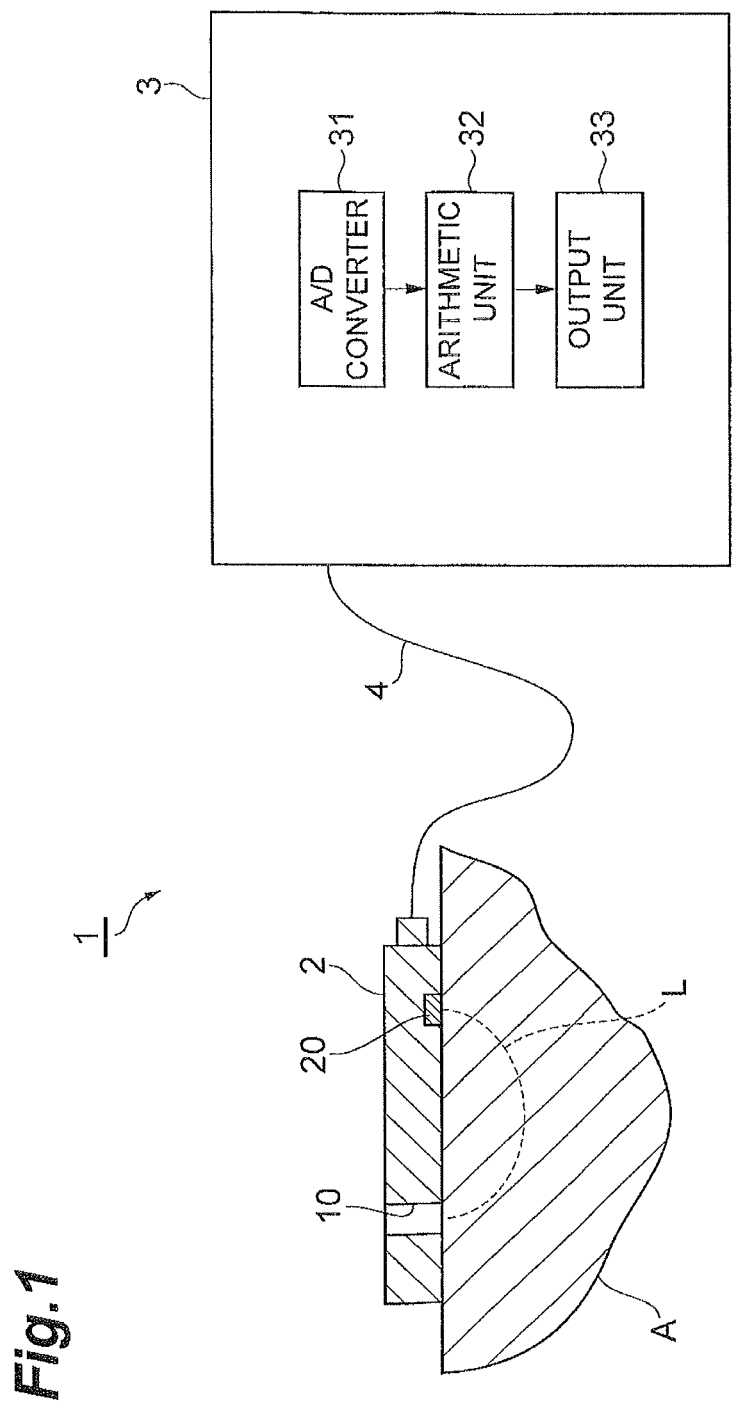

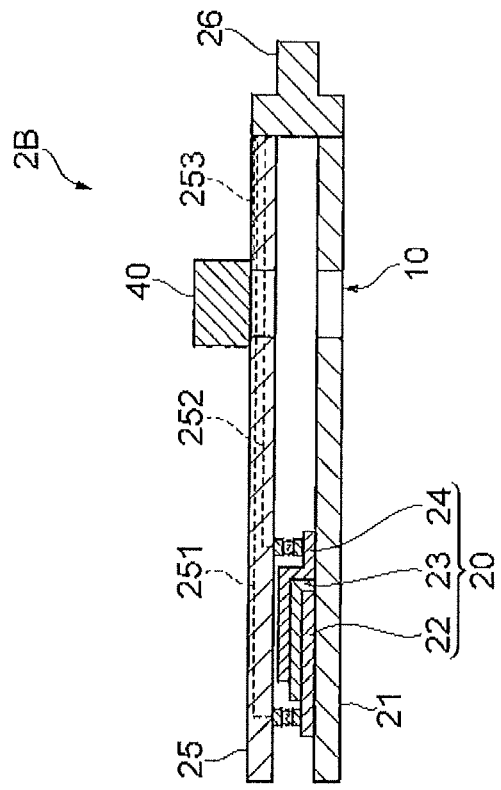
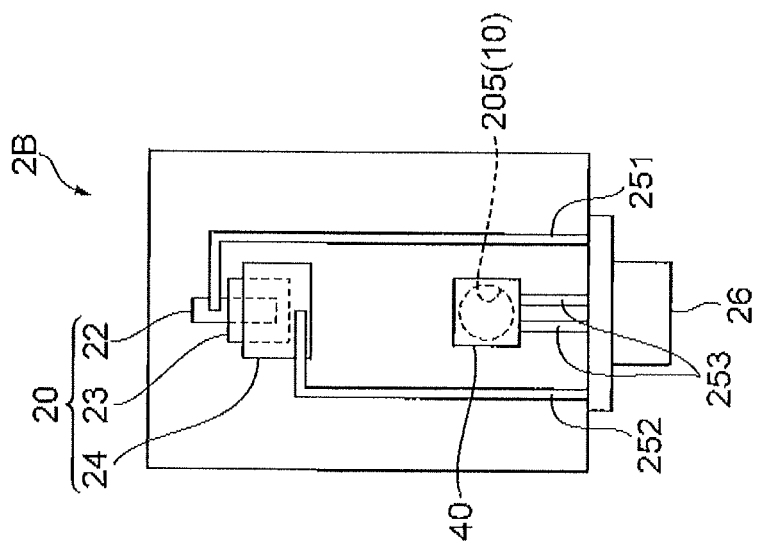
Fig.4A
Fig.4B

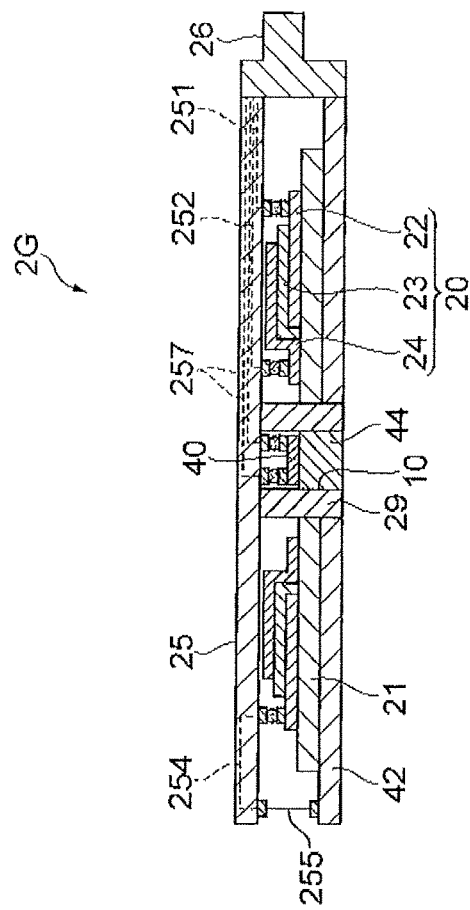
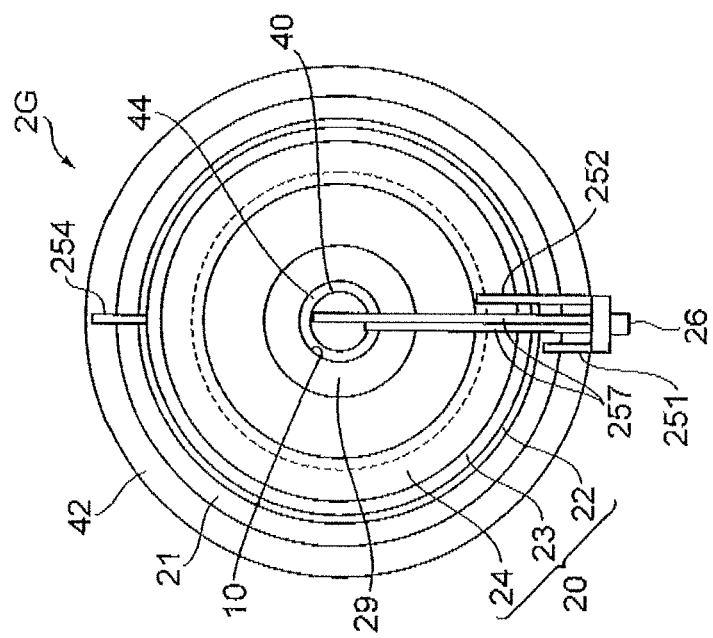

PROBE FOR BIOINSTRUMENTATION AND BIOINSTRUMENTATION DEVICE

TECHNICAL FIELD

The present invention relates to a probe for bioinstrumentation and a bioinstrumentation device using the probe for bioinstrumentation.

BACKGROUND

In a conventionally known device that radiates light onto a living body and detects light emitted from the living body to evaluate a health condition, for example, of the living body, use of an optical photo detector (OPD) using an organic semiconductor has been studied in recent years.

The OPD can be formed on a flexible substrate, and thus is very useful for measurement of a living body having a curved surface. For example, Patent Document 1 describes a pulse sensor in which a light source and an organic light-receiving element are provided on a flexible substrate.

Patent Document 1: Japanese Patent Application Laid-Open Publication No. 2008-103670

SUMMARY

However, with the configuration of the pulse sensor described in Patent Application Laid-Open Publication No. 2008-103670, there is a possibility that light other than light emitted from a living body is also received, and thus it is desired to detect light from an irradiated body at higher accuracy.

Furthermore, not only in pulse measurement but also in all aspects of bioinstrumentation using light, light other than light emitted from a living body causes noise, thereby inhibiting accurate measurement.

The present invention has been made in view of the foregoing, and an object thereof is to provide a probe for bioinstrumentation that can accurately detect light from a living body and a bioinstrumentation device including the probe for bioinstrumentation.

To achieve the above-described object, a probe for bioinstrumentation according to one aspect of the present invention includes: a transparent substrate having flexibility; an organic light-receiving element that is provided on the transparent substrate, has an organic photoelectric-conversion layer sandwiched between a transparent electrode and an upper electrode, and, when light for measurement is radiated onto a subject, detects scattered light that is scattered by the subject; an upper circuit board that has flexibility and is provided on the side opposite to the transparent substrate with respect to the organic light-receiving element, and is provided with wires therein that are connected with the transparent electrode and the upper electrode; a projection optical path that is provided apart from the organic light-receiving element and transmits light for measurement along a thickness direction of the transparent substrate; and a connector that is attached to the upper circuit board and allows the wires to be externally connected, wherein the upper electrode has a light-blocking effect and covers an end of the organic photoelectric-conversion layer on the side of the projection optical path.

In the above-described probe for bioinstrumentation, the end of the organic photoelectric-conversion layer on the side of the projection optical path is covered by the upper electrode having a light-blocking effect, whereby light from a light source passing through the projection optical path can be prevented from directly entering the organic photoelectric-conversion layer. Thus, the organic photoelectric-conversion layer can be prevented from receiving light different from the scattered light from the subject, so that light from the subject can be accurately detected.

Herein, a mode including a light-blocking member that is provided, to block light from the projection optical path, between the projection optical path and the organic light-receiving element may be possible.

In this case, the light-blocking member can effectively prevent light from the projection optical path from being detected by the organic light-receiving element, and thus light from the subject can be more accurately detected.

Another mode in which the projection optical path is formed as a through hole penetrated through the probe for bioinstrumentation in a thickness direction thereof and a light source is provided, to emit the light for measurement, on the upper circuit board at the upper end of the through hole may be possible.

Yet another mode in which the probe for bioinstrumentation further includes an organic light-emitting diode (LED) that is provided, to emit the light for measurement, on the transparent substrate apart from the organic light-receiving element and the projection optical path is formed in the transparent substrate under the organic LED may be possible.

When the organic LED is included as the light source on the transparent substrate, the projection optical path is shorter than that in the case when the light source is provided above the projection optical path penetrating the probe for bioinstrumentation, and thus the possibility that light from the light source is directly detected by the organic light-receiving element can be further reduced.

Yet another mode in which the organic light-receiving element is formed in a ring-shaped manner and the projection optical path is provided in a central portion inside the organic light-receiving element may be possible.

By arranging the organic light-receiving element in a ring-shaped manner as described above, scattered light from the subject can be efficiently received, whereby detection can be accurately performed. Furthermore, forming a ring-shaped light-receiving element with the organic light-receiving element can reduce the possibility that light between neighboring light-receiving elements cannot be detected, for example, in comparison with the case when a plurality of light-receiving elements of what is called inorganic material are arranged in a ring-shaped manner, thereby enabling detection to be more accurately performed.

A bioinstrumentation device according to one aspect of the present invention includes: the above-described probe for bioinstrumentation; a cable that is connected with a connector of the probe for bioinstrumentation; and a measurement unit that is connected with the probe for bioinstrumentation through the cable and acquires information on the inside of the subject based on a detection signal from the organic light-receiving element of the probe for bioinstrumentation.

With the above-described bioinstrumentation device, light from the light source passing through the projection optical path is prevented from directly entering the organic photoelectric-conversion layer in the probe for bioinstrumentation, so that light different from scattered light from the subject can be prevented from being received by the organic photoelectric-conversion layer, whereby the light from the subject can be accurately detected.

The present invention makes it possible to provide a probe for bioinstrumentation that can accurately detect light from a living body and a bioinstrumentation device including the probe for bioinstrumentation.

BRIEF DESCRIPTION OF THE DRAWINGS

FIG. 1 is a schematic block diagram of a bioinstrumentation device according to a first embodiment.

FIG. 4A is a plan view of a probe for bioinstrumentation constituting a bioinstrumentation device according to a third embodiment, and FIG. 4B is a sectional view corresponding to FIG. 2B.

FIG. 9A is a plan view of a probe for bioinstrumentation constituting a bioinstrumentation device according to an eighth embodiment, and FIG. 9B is a sectional view corresponding to FIG. 2B.

DETAILED DESCRIPTION

Embodiments of the present invention will be described hereinafter in detail with reference to the accompanying drawings. In descriptions of the drawings, like numerals refer to like or equivalent elements, and duplicated explanations are omitted.

First Embodiment

Figure 2A:
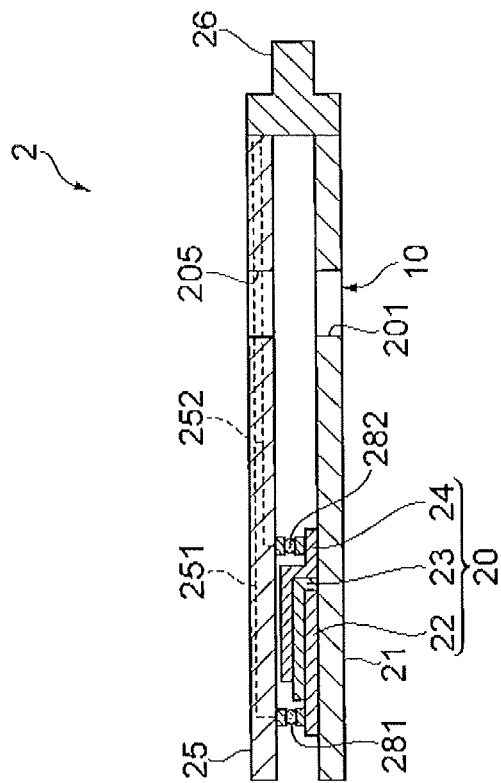
FIG. 2A is a plan view of a probe for bioinstrumentation constituting the bioinstrumentation device according to the first embodiment.
Figure 2B:
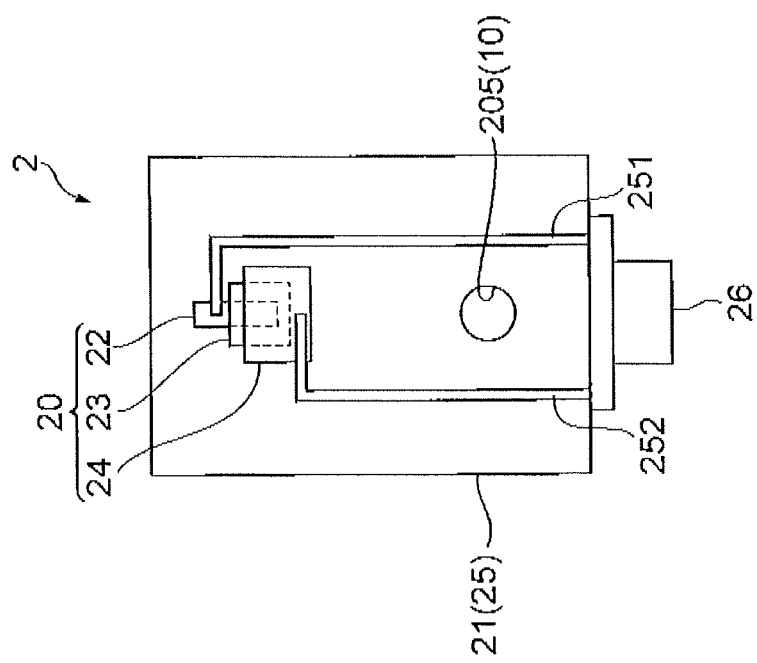
FIG. 2B is a sectional view along line II-II indicated in FIG. 2A.

FIG. 1 is a schematic block diagram of a bioinstrumentation device according to a first embodiment of the present invention. FIG. 2A is a plan view of a probe for bioinstrumentation constituting the bioinstrumentation device according to the first embodiment, and FIG. 2B is a sectional view along line II-II indicated in FIG. 2A.

As depicted in FIG. 1, this bioinstrumentation device 1 has a configuration in which a probe 2 (probe for bioinstrumentation) and a measurement unit 3 are connected via a cable 4. This bioinstrumentation device 1 is a device that radiates light onto a subject as a living body to detect scattered light from the subject, thereby acquiring information on the inside of the subject. Examples of the information on the inside of the subject include oxyhemoglobin concentration, deoxyhemoglobin concentration, total hemoglobin concentration, arterial oxygen saturation, oxygen saturation of mixed arterial and venous blood, normalized tissue hemoglobin index, myoglobin concentration, cytochrome oxidase concentration, melanin concentration, glucose concentration, lactate concentration, water content, and fat content. In the embodiments below, a case will be described in which the bioinstrumentation device 1 is a device that measures the oxyhemoglobin concentration and the deoxyhemoglobin concentration in a living-body tissue.

As depicted in FIG. 1, the probe 2 is secured on a surface of a subject A when used, and causes light from a light source to enter the subject A via a projection optical path 10. The light source can include a semiconductor light-emitting element such as a light-emitting diode (LED), but may be provided separately from the bioinstrumentation device 1. The light intensity of light L that is the resulting light after entering the subject A from the projection optical path 10 and being transmitted inside the subject A is detected by an organic light-receiving element unit 20 arranged at about several centimeters of distance from the projection optical path 10. According to the light intensity, an electrical detection signal is generated, and transmitted to the measurement unit 3 via the cable 4.

The measurement unit 3 includes an A/D converter 31, an arithmetic unit 32, and an output unit 33. The A/D converter 31 is means for converting the detection signal transmitted from the organic light-receiving element unit 20 from an analog signal to a digital signal. The detection signal converted by the A/D converter 31 is sent to the arithmetic unit 32.

The arithmetic unit 32 calculates the oxygen saturation of hemoglobin contained in the living body on the basis of the detection signal received from the A/D converter 31. Data representing the oxyhemoglobin concentration and the deoxyhemoglobin concentration calculated by the arithmetic unit 32 is sent to the output unit 33.

The output unit 33 outputs the oxyhemoglobin concentration and the deoxyhemoglobin concentration sent from the arithmetic unit 32 to a display, for example. Accordingly, the result of calculation performed by the arithmetic unit 32 is notified of a user of the bioinstrumentation device 1.

In addition, when the bioinstrumentation device 1 includes a light source, the bioinstrumentation device 1 further includes a function unit that controls light emitted from the light source.

The above-described functions in the bioinstrumentation device 1 are implemented by a system including a CPU, a RAM and a ROM as main storages, a communication module, auxiliary storages exemplified by a hard disk and a flash memory, an input device exemplified by a keyboard, and an output device such as a display.

The following describes the probe 2 according to the present embodiment with reference to FIG. 2. As depicted in FIG. 2, the probe 2 includes a transparent substrate 21, a transparent electrode 22 (lower electrode), an organic photoelectric-conversion layer 23, an upper electrode 24, an upper circuit board 25, and a connector 26. In FIG. 2A, the upper circuit board 25 is omitted to illustrate the inner configuration more specifically.

The transparent substrate 21 in a rectangular shape is made of flexible material so that the probe 2 can be secured on a surface, for example, of the subject A. As the transparent substrate 21, for example, polyethylene terephthalate (PET) can be used. The transparent substrate 21 has light transparency. The term "has light transparency" herein means that the transmittance of light having a target wavelength is equal to or higher than 60%. The light having a target wavelength is light that is used when measurement with the probe 2 is performed and is to be detected in the organic light-receiving element unit 20.

On the transparent substrate 21, the transparent electrode 22 that functions as a lower electrode is formed. The transparent electrode 22 can be formed by depositing indium-tin oxide (ITO), for example. The transparent electrode 22 also has light transparency similarly to the transparent substrate 21.

The organic photoelectric-conversion layer 23 is formed on the transparent electrode 22. The organic photoelectric-conversion layer 23 can be made of a p-type organic semiconductor PCPDTBT (cyclopentadithiophene derivative) and an n-type organic semiconductor PCBM (fullerene derivative). The organic photoelectric-conversion layer 23 can be formed on the transparent substrate 21 by a printing process, for example.

The upper electrode 24 is formed above the organic photoelectric-conversion layer 23. The upper electrode 24 can be made of metallic material having a light-blocking effect and, for example, aluminum can be used therefor. The term "having a light-blocking effect" herein means that light of a wavelength to which the organic photoelectric-conversion layer has sensitivity can be blocked by 60% or more. Examples of the material having a light-blocking effect include a material that can reflect 60% or more of the light to which the organic photoelectric-conversion layer has sensitivity. The organic light-receiving element unit 20 (organic light-receiving element) is constructed of the transparent electrode 22, the organic photoelectric-conversion layer 23, and the upper electrode 24 described above. The periphery of the organic light-receiving element unit 20 may be sealed with a filler having light transparency, for example.

The upper circuit board 25 has a rectangular shape similar to that of the transparent substrate 21, and is made of material having a light-blocking effect and flexibility such as a metal-coated polyimide film. The upper circuit board 25 is provided in a position overlapping the transparent substrate 21 above the upper electrode 24. An end of the upper circuit board 25 is connected with the transparent substrate 21 through the connector 26 that is externally connectable. Inside the upper circuit board 25, a wire 251 that extends from the connector 26 and connects the connector 26 with the transparent electrode 22 and a wire 252 that extends from the connector 26 and connects the connector 26 with the upper electrode 24 are provided. When connected with the cable 4 through the connector 26, the transparent electrode 22 and the upper electrode 24 are connected to the measurement unit 3 via the wires 251 and 252 and the cable 4. The connector 26 only has to be attached to at least the upper circuit board 25, and does not have to be attached to the transparent substrate 21.

FIG. 2B illustrates a configuration in which the transparent substrate 21 and the upper circuit board 25 are arranged apart from each other. However, because flexible material is used for the upper circuit board 25, the upper circuit board 25 can be made closer to the transparent substrate 21 that is similarly flexible when the probe 2 is assembled. In this case, the connector 26 may fix together the transparent substrate 21 and the upper circuit board 25 in such a state that the upper circuit board 25 is stacked on the transparent substrate 21. Herein, a gap between the transparent substrate 21 and the upper circuit board 25 may be filled with a filler so that the shape as depicted in FIG. 2B (state in which the transparent substrate 21 and the upper circuit board 25 are apart from each other) is maintained.

In the transparent substrate 21 and the upper circuit board 25, through holes 201 and 205 are respectively formed at positions overlapping each other when viewed from above. Through these two through holes 201 and 205, the projection optical path 10 that penetrates from the top (upper side of the upper circuit board 25) to the bottom (lower side of the transparent substrate 21) of the probe 2 in the thickness direction of the transparent substrate 21 (thickness direction of the probe 2) is formed. Accordingly, when an external light source for bioinstrumentation is attached to the upper end (above the upper circuit board 25) of the projection optical path 10 with the probe 2 being secured on a surface of the subject (see FIG. 1), light from the light source can be radiated on the surface of the subject A via the projection optical path 10.

In the transparent electrode 22 herein, as depicted in FIG. 2A when the probe 2 is viewed from above, an area is formed that is exposed without overlapping the organic photoelectric-conversion layer 23 or the upper electrode 24. Specifically, in the transparent electrode 22, an area containing an end opposite to the side of the projection optical path 10 is exposed. In this exposed area, the wire 251 in the upper circuit board 25 is connected with the transparent electrode 22 through a bump 281.

The organic photoelectric-conversion layer 23 is provided so as to cover an area of the upper surface of the transparent electrode 22 that is different from the area in which the bump 281 is provided and an end face of the transparent electrode 22 on the projection optical path 10 side.

Furthermore, the upper electrode 24 is provided so as to cover the upper surface of the organic photoelectric-conversion layer 23 and an end of the organic photoelectric-conversion layer 23 on the projection optical path 10 side. An end of the upper electrode on the projection optical path 10 side covers the end face of the organic photoelectric-conversion layer 23 on the projection optical path 10 side and also extends on the transparent substrate 21, and is connected with the wire 252 in the upper circuit board 25 through a bump 282 in an area that does not overlap the transparent electrode 22 or the organic photoelectric-conversion layer 23 when the probe 2 is viewed from above.

In this probe 2, the end face of the organic photoelectric-conversion layer 23 on the projection optical path 10 side is covered by the upper electrode 24 having a light-blocking effect, whereby light passing through the projection optical path 10 from the light source can be prevented from directly entering the organic photoelectric-conversion layer 23. Accordingly, the organic photoelectric-conversion layer 23 can be prevented from receiving light that is different from scattered light incident from the subject A via the transparent substrate 21 and the transparent electrode 22, whereby the light incident from the subject A can be accurately detected.

The "end" of the organic photoelectric-conversion layer 23 that is covered by the upper electrode 24 having a light-blocking effect is an area containing at least the end face thereof on the projection optical path 10 side. It is preferable that the upper surface of the organic photoelectric-conversion layer 23 be covered by the upper electrode.

Second Embodiment

Figure 3B:
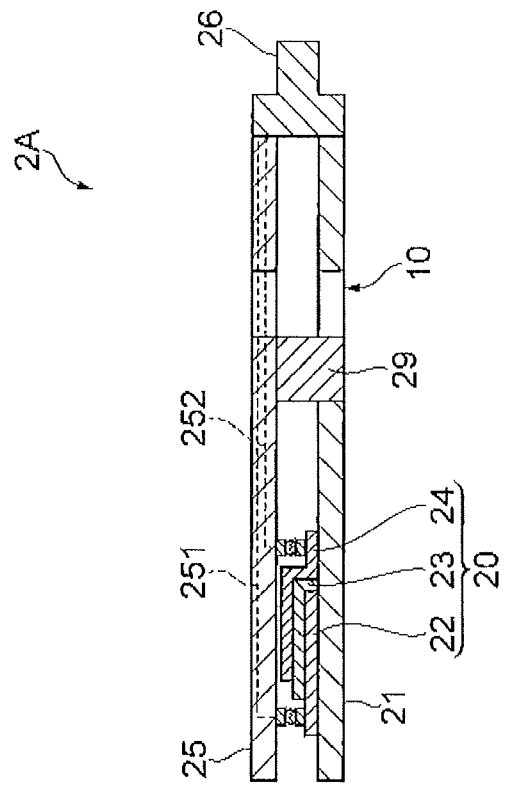
FIG. 3B is a sectional view corresponding to FIG. 2B.
Figure 3A:
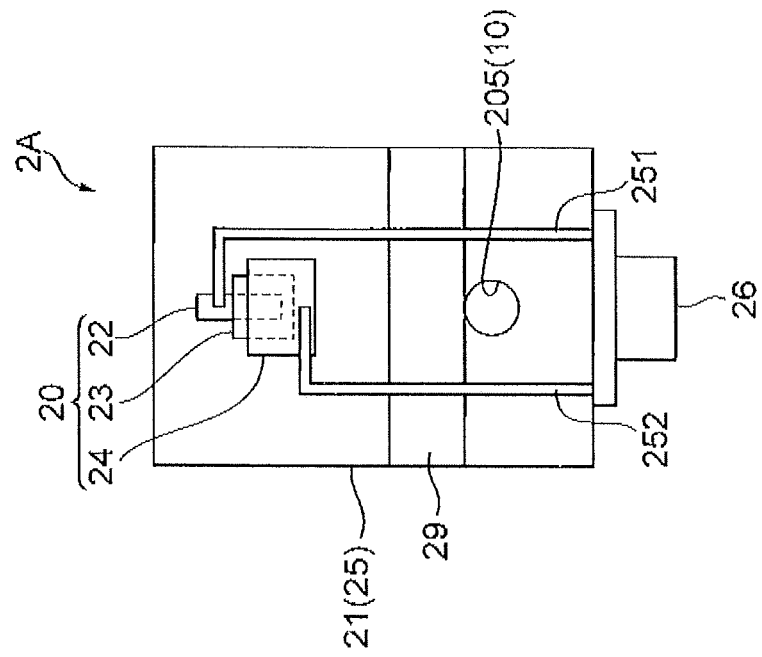
FIG. 3A is a plan view of a probe for bioinstrumentation constituting a bioinstrumentation device according to a second embodiment.

The following describes a probe 2A according to a second embodiment with reference to FIG. 3. FIG. 3A is a plan view of a probe for bioinstrumentation constituting a bioinstrumentation device according to the second embodiment, and FIG. 3B is a sectional view corresponding to FIG. 2B.

The probe 2A according to the second embodiment is different in configuration from the probe 2 according to the first embodiment as follows. Specifically, a light-blocking member 29 is provided between the projection optical path 10 and the organic light-receiving element unit 20 constructed of the transparent electrode 22, the organic photo-electric-conversion layer 23, and the upper electrode 24.

The light-blocking member 29 is provided so as to partition an area below the upper circuit board 25 between the projection optical path 10 and the organic light-receiving element unit 20 as depicted in FIG. 3B. More specifically, the light-blocking member 29 is provided so as to form a part of a side wall of the projection optical path 10. Furthermore, the light-blocking member 29 is provided so as to partition the transparent substrate 21 between the projection optical path 10 and the organic light-receiving element unit 20 as depicted in FIG. 3A. Because the light-blocking member 29 is provided between the projection optical path 10 and the organic light-receiving element unit 20 in this manner, light passing through the projection optical path 10 from the light source can be more effectively prevented from directly entering the organic photoelectric-conversion layer 23, so that light from the subject A can be more accurately detected.

In the probe 2A according to the second embodiment, because the transparent substrate 21 on the projection optical path 10 side and the transparent substrate 21 on the organic light-receiving element unit 20 side are separated by the light-blocking member 29, light from the light source can also be prevented from being transmitted in the transparent substrate 21 and reaching the organic light-receiving element unit 20.

The shape of the light-blocking member 29 can be changed as appropriate. The light-blocking member 29 is provided so as to cover at least a part of an area that can be an optical path between the projection optical path 10 and the organic light-receiving element unit 20, whereby the ratio of light from the light source that directly reaches the organic light-receiving element unit 20 can be reduced, so that light from the subject A can be more accurately detected. The light-blocking member 29 may be provided apart from the projection optical path 10 so that the transparent substrate 21 lies between the light-blocking member 29 and the projection optical path 10. The light-blocking member 29 may cover the whole periphery of the projection optical path 10.

Third Embodiment

The following describes a probe 2B according to a third embodiment with reference to FIG. 4. FIG. 4A is a plan view of a probe for bioinstrumentation constituting a bioinstrumentation device according to the third embodiment, and FIG. 4B is a sectional view corresponding to FIG. 2B.

The probe 2B according to the third embodiment is different in configuration from the probe 2 according to the first embodiment as follows. Specifically, a light source 40 is fixed on the upper circuit board 25 at the upper end of the projection optical path 10 so as to cover the projection optical path 10. The light source 40 is connected with the connector 26 through a wire 253 in the upper circuit board 25.

The light source 40 may be an inorganic-semiconductor light source, or may be an organic light-emitting element. Examples of the inorganic-semiconductor light source include a surface-emitting LED. Examples of the organic light-emitting element include an organic LED. In particular, among these, it is preferable to use the organic light-emitting element. Because the organic LED can be formed as a thin film on a flexible substrate, a structure can be fabricated that is advantageous in flexibility for the probe as a whole.

In this manner, the light source 40 may be attached to the probe 2B. In this case, light emitted from the light source 40 is controlled by the measurement unit 3.

Fourth Embodiment

Figure 5A:
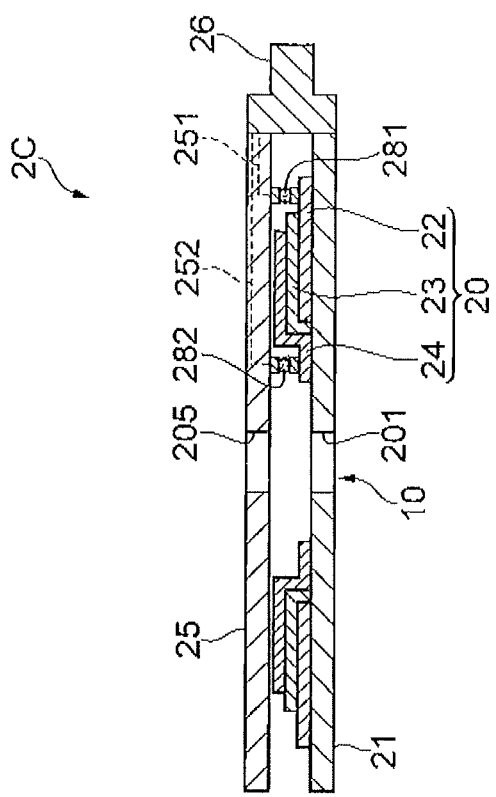
FIG. 5A is a plan view of a probe for bioinstrumentation constituting a bioinstrumentation device according to a fourth embodiment.
Figure 5B:
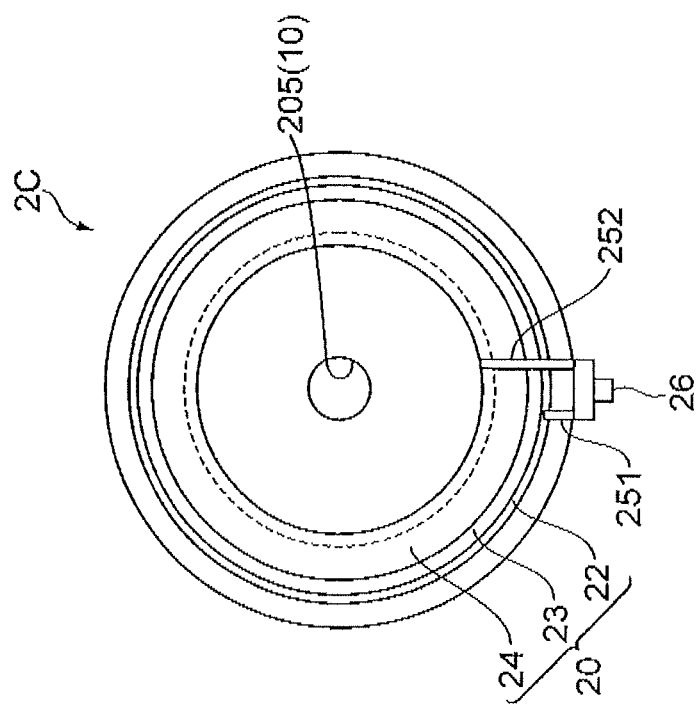
FIG. 5B is a sectional view corresponding to FIG. 2B.

The following describes a probe 2C according to a fourth embodiment with reference to FIG. 5. FIG. 5A is a plan view of a probe for bioinstrumentation constituting a bioinstrumentation device according to the fourth embodiment, and FIG. 5B is a sectional view corresponding to FIG. 2B.

The probe 2C according to the fourth embodiment is different in configuration from the probe 2 according to the first embodiment as follows. Specifically, the probe has a circular shape and in the central portion thereof, the projection optical path 10 is provided.

As specifically described below, the transparent substrate 21 having a circular shape and flexibility and the upper circuit board 25 similarly having a circular shape and flexibility overlap each other in the thickness direction. In the central portion thereof, the projection optical path 10 is provided that is formed as the through holes 201 and 205 and extends in the thickness direction. In addition, the organic light-receiving element unit 20 having an annular shape is provided outside and apart from the projection optical path 10. The transparent electrode 22, the organic photoelectric-conversion layer 23, and the upper electrode 24 that constitute the organic light-receiving element unit 20 are stacked on the transparent substrate 21 upward in this order. The transparent substrate 21 and the upper circuit board 25 in a circular shape are fixed together at one position of the periphery thereof by the connector 26.

In this case, similarly to the probe 2, in the transparent electrode 22, as depicted in FIG. 5A when the probe 2C is viewed from above, an area that is exposed without overlapping the organic photoelectric-conversion layer 23 or the upper electrode 24 is formed on the outer peripheral side of the transparent electrode 22 in a circular shape. In this exposed area, the wire 251 in the upper circuit board 25 is connected with the transparent electrode 22 through the bump 281 near the connector 26.

The organic photoelectric-conversion layer 23 is provided so as to cover an end face of the upper surface of the transparent electrode 22 on the inner peripheral side. Furthermore, the upper electrode 24 is provided so as to cover the upper surface of the organic photoelectric-conversion layer 23 and an end face of the organic photoelectric-conversion layer 23 on the projection optical path 10 side. The end of the upper electrode on the projection optical path 10 side covers the end face (inner peripheral surface) of the organic photoelectric-conversion layer 23 on the projection optical path 10 side and also extends on the transparent substrate 21, and is connected with the wire 252 in the upper circuit board 25 through the bump 282 in an area that does not overlap the transparent electrode 22 or the organic photoelectric-conversion layer 23 when the probe 2C is viewed from above.

In the probe 2C, the end face (inner peripheral surface) of the organic photoelectric-conversion layer 23 on the projection optical path 10 side is covered by the upper electrode 24 having a light-blocking effect, whereby light passing through the projection optical path 10 from the light source can be prevented from directly entering the organic photoelectric-conversion layer 23. Accordingly, the organic photoelectric-conversion layer 23 can be prevented from receiving light that is different from scattered light incident from the subject A via the transparent substrate 21 and the transparent electrode 22, whereby the light incident from the subject A can be accurately detected.

Because the wires 251 and 252 that electrically connect the transparent electrode 22 and the upper electrode 24 with the connector 26 are housed in the upper circuit board 25, it is possible to prevent the light intensity of light received by the organic light-receiving element unit 20 from being reduced by forming the wires on the transparent substrate 21, for example. Thus, light from the subject A can be accurately detected.

If an inorganic light-receiving element is used as the light-receiving surface having an annular shape, a plurality of chips need to be arranged in a ring shape. In this case, gaps are generated between the neighboring chips, which makes it difficult by any means to arrange all elements around the projection optical path 10. In contrast, when the organic light-receiving element unit 20 is used as in the probe 2C, the organic light-receiving element unit 20 only has to be formed in an annular shape, and thus light from the subject A can be received without leakage.

In the above-described embodiment, a configuration has been described in which the organic light-receiving element unit 20 has an annular shape. However, the organic light-receiving element unit 20 does not have to have a shape of a complete annular ring, and may have a structure in which a part thereof is missing (discontinuous). The organic light-receiving element unit 20 only has to be formed in what is called a ring shape, and the shape may be changed from the annular shape.

Fifth Embodiment

Figure 6B:
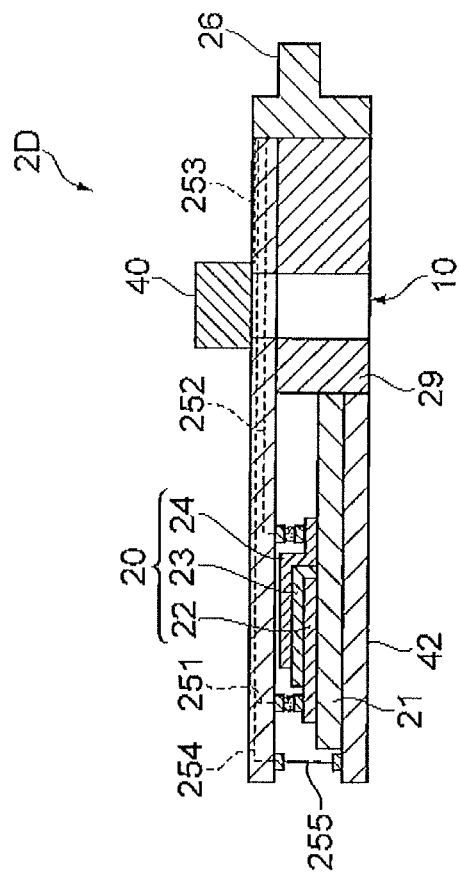
FIG. 6B is a sectional view corresponding to FIG. 2B.
Figure 6A:
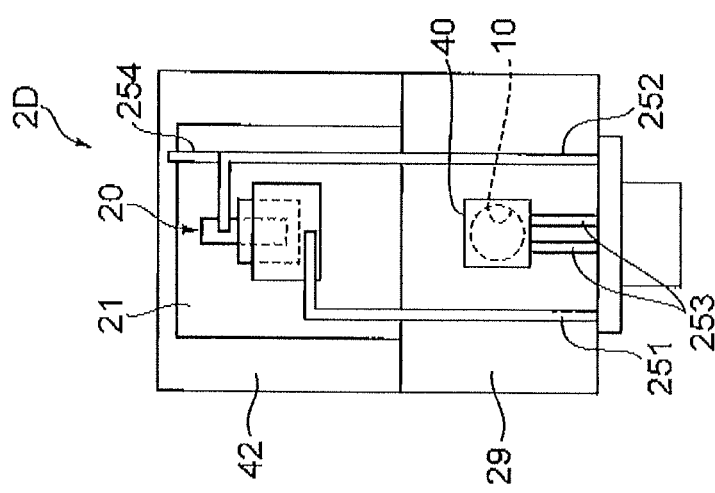
FIG. 6A is a plan view of a probe for bioinstrumentation constituting a bioinstrumentation device according to a fifth embodiment.

The following describes a probe 2D according to a fifth embodiment with reference to FIG. 6. FIG. 6A is a plan view of a probe for bioinstrumentation constituting a bioinstrumentation device according to the fifth embodiment, and FIG. 6B is a sectional view corresponding to FIG. 2B.

The probe 2D according to the fifth embodiment is different in configuration from the probe 2 according to the first embodiment as follows. Specifically, the probe 2D is different in that a conductive film having flexibility and light transparency is provided below the transparent substrate 21, that the periphery of the projection optical path 10 is covered by the light-blocking member 29, and that the light source 40 is fixed on the upper circuit board 25 at the upper end of the projection optical path 10 so as to cover the projection optical path 10.

In the probe 2, the transparent substrate 21 and the upper circuit board 25 have approximately the same shape, and overlap each other when being viewed from above. By contrast, in the probe 2D, the transparent substrate 21 is smaller than the upper circuit board 25, and a conductive film 42 provided below the transparent substrate 21 is electrically connected with the transparent electrode 22 through the wire 254 in the upper circuit board 25 and a wire 255 extending from the wire 254 (see FIG. 6B). As the conductive film 42, a PET film on which ITO is deposited or a PET film on which thin metallic wires are formed, for example, can be used. In this manner, the conductive film 42 that is electrically connected via the wires is provided below the organic light-receiving element unit 20, whereby effect of external electromagnetic noise in the organic light-receiving element unit 20 can be reduced, so that accuracy of detecting light from the subject A can be increased.

The light-blocking member 29 of the probe 2D surrounds the whole periphery of the projection optical path 10. The light-blocking member 29 is provided between the projection optical path 10 and the organic light-receiving element unit 20, whereby light passing through the projection optical path 10 from the light source 40 can be more effectively prevented from directly entering the organic photoelectric-conversion layer 23, so that light from the subject A can be more accurately detected. Because the projection optical path 10 and the organic light-receiving element unit 20 are not connected through a member having light transparency such as the transparent substrate 21, light from the light source 40 can also be prevented from being transmitted through the transparent substrate 21 and reaching the organic light-receiving element unit 20.

Sixth Embodiment

Figure 7A:
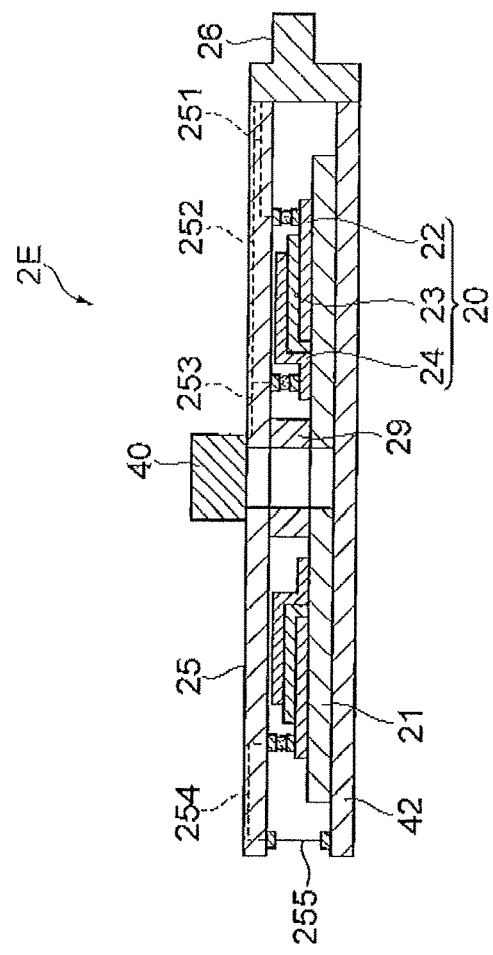
FIG. 7A is a plan view of a probe for bioinstrumentation constituting a bioinstrumentation device according to a sixth embodiment.
Figure 7B:
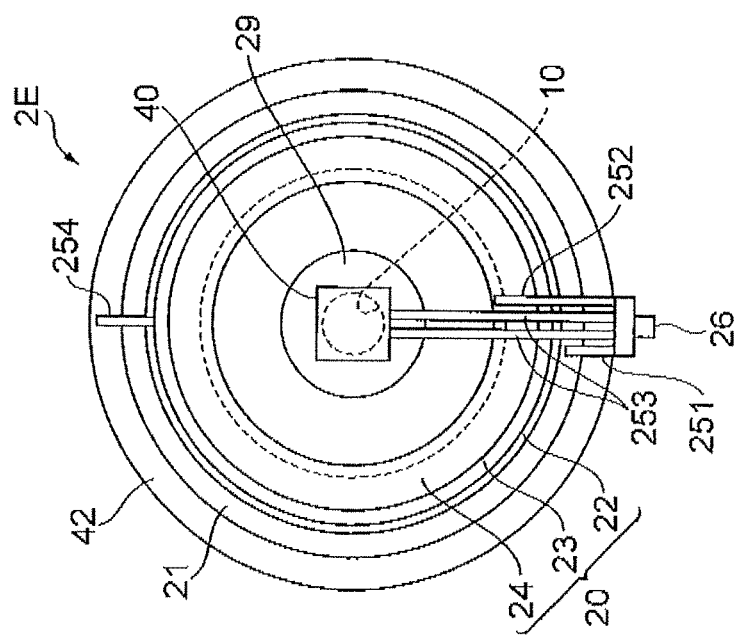
FIG. 7B is a sectional view corresponding to FIG. 2B.

The following describes a probe 2E according to a sixth embodiment with reference to FIG. 7. FIG. 7A is a plan view of a probe for bioinstrumentation constituting a bioinstrumentation device according to the sixth embodiment, and FIG. 7B is a sectional view corresponding to FIG. 2B.

The probe 2E according to the sixth embodiment is different in configuration from the probe 2C having a circular shape according to the fourth embodiment as follows. Specifically, similarly to the probe 2D according to the fifth embodiment, the probe 2E is different in that a conductive film having flexibility is provided below the transparent substrate 21, that the periphery of the projection optical path 10 is covered by the light-blocking member 29, and that the light source 40 is fixed on the upper circuit board 25 at the upper end of the projection optical path 10 so as to cover the projection optical path 10.

In the probe 2E, the transparent substrate 21 is smaller than the upper circuit board 25. In a position where the conductive film 42 provided below the transparent substrate 21 does not overlap the transparent substrate 21, the conductive film 42 is electrically connected with the transparent substrate 21 through the wire 254 in the upper circuit board 25 and the wire 255 extending from the wire 254. In this manner, the conductive film 42 that is electrically connected via the wires is provided below the organic light-receiving element unit 20, whereby effect of external electromagnetic noise in the organic light-receiving element unit 20 can be reduced, so that accuracy of detecting light from the subject A can be increased.

The light-blocking member 29 of the probe 2E surrounds the whole periphery of the projection optical path 10. The light-blocking member 29 is provided between the projection optical path 10 and the organic light-receiving element unit 20, whereby light passing through the projection optical path 10 from the light source can be more effectively prevented from directly entering the organic photoelectric-conversion layer 23, so that light from the subject A can be more accurately detected. Because the projection optical path 10 and the organic light-receiving element unit 20 are not connected through a member having light transparency such as the transparent substrate 21, light from the light source can also be prevented from being transmitted through the transparent substrate 21 and reaching the organic light-receiving element unit 20.

Seventh Embodiment

Figure 8A:
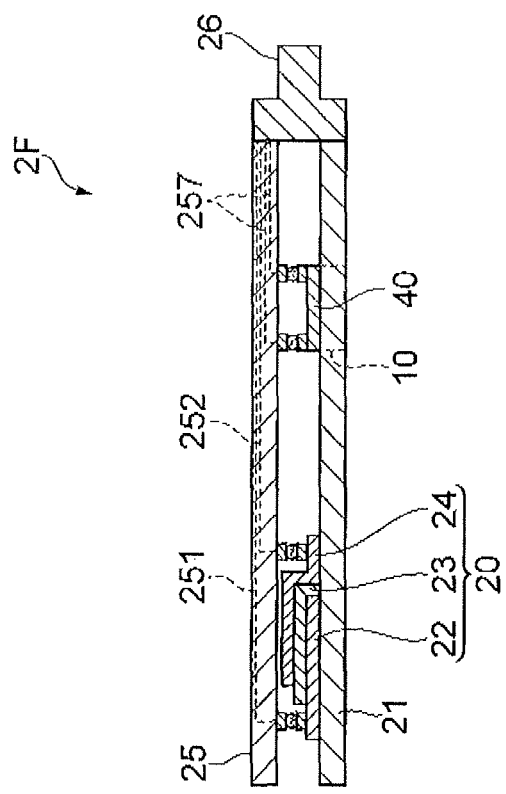
FIG. 8A is a plan view of a probe for bioinstrumentation constituting a bioinstrumentation device according to a seventh embodiment.
Figure 8B:
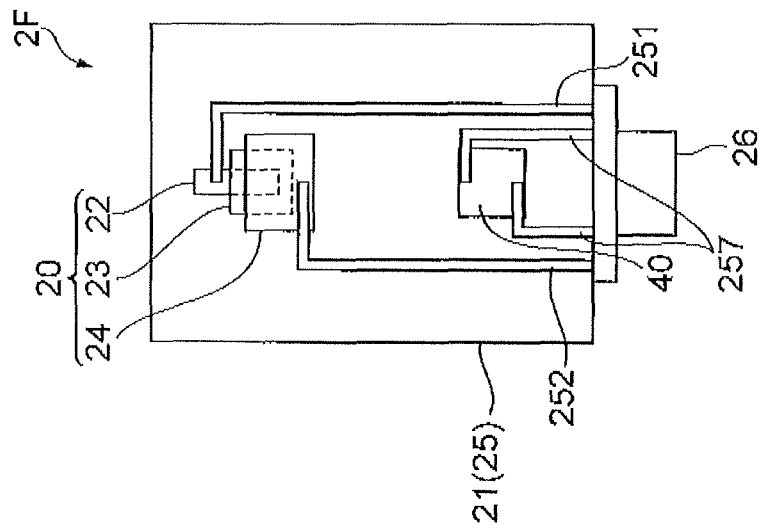
FIG. 8B is a sectional view corresponding to FIG. 2B.

The following describes a probe 2F according to a seventh embodiment with reference to FIG. 8. FIG. 8A is a plan view of a probe for bioinstrumentation constituting a bioinstrumentation device according to the seventh embodiment, and FIG. 8B is a sectional view corresponding to FIG. 2B.

The probe 2F according to the seventh embodiment is different in configuration from the probe 2 according to the first embodiment as follows. Specifically, the probe 2F is different in that an organic LED is provided on the transparent substrate 21 as the light source 40. In this case, the transparent substrate 21 under the light source 40 functions as the projection optical path 10. As depicted in FIG. 8, the light source 40 may be provided on a transparent substrate 21 that is the same as the transparent substrate 21 on which the organic light-receiving element unit 20 is provided, or may be provided on a transparent substrate 21 that is prepared separately from the transparent substrate 21 on which the organic light-receiving element unit 20 is provided. When the light source 40 is attached on the transparent substrate 21 that is prepared separately, connecting the two transparent substrates through a material having a light-blocking effect can prevent light from being transmitted between the two transparent substrates.

The light source 40 is connected with the connector 26 via a wire 257 provided in the upper circuit board 25, and thus can be connected to the measurement unit 3 of the bioinstrumentation device 1 via the cable 4. This connection enables emission of light from the light source 40 to be controlled based on control signals from the measurement unit 3.

In this manner, the light source 40 may be placed on the transparent substrate without forming the projection optical path. In this case also, the upper electrode 24 having a light-blocking effect is provided on the light source 40 side, whereby light from the light source 40 can be prevented from being detected directly by the organic light-receiving element unit 20.

When an organic LED is used as the light source 40, the length of the projection optical path is shorter than that in the case when the light source is provided above the projection optical path penetrating the probe for bioinstrumentation, and thus the possibility that light from the light source is directly detected by the organic light-receiving element can be further reduced. Furthermore, because the organic LED can be formed as a thin film on a flexible substrate, a structure can be fabricated that is advantageous in flexibility of the probe as a whole.

Eighth Embodiment

The following describes a probe 2G according to an eighth embodiment with reference to FIG. 9. FIG. 9A is a plan view of a probe for bioinstrumentation constituting a bioinstrumentation device according to the eighth embodiment, and FIG. 9B is a sectional view corresponding to FIG. 2B.

The probe 2G according to the eighth embodiment is different in configuration from the probe 2E having a circular shape according to the sixth embodiment as follows. Specifically, similarly to the probe 2F according to the seventh embodiment, the probe 2G is different in that an organic LED is used as the light source 40 and further this organic LED is arranged in the projection optical path 10.

In the probe 2G, similarly to the probe 2E, the periphery of the projection optical path 10 formed in the center of the probe 2G having a circular shape is covered by the light-blocking member 29. In addition to the transparent substrate 21 on which the organic light-receiving element unit 20 is provided, a transparent substrate 44 is provided in the projection optical path 10, and an organic LED as the light source 40 is attached on the upper surface of the transparent substrate 44. In probe 2G, similarly to the probe 2E, the transparent substrate 21 is smaller than the upper circuit board 25. In a position where the conductive film 42 provided below the transparent substrate 21 does not overlap the transparent substrate 21, the conductive film 42 is electrically connected with the wire 254 in the upper circuit board 25 and the wire 255 extending from the wire 254.

In this manner, also in the probe 2G having a circular shape, the light source 40 can be placed on the transparent substrate. In this case, the upper electrode 24 having a light-blocking effect is provided on the light source 40 side, whereby light from the light source 40 can be prevented from being detected directly by the organic light-receiving element unit 20. In the probe 2G, because the transparent substrate 44 on which the light source 40 is attached and the transparent substrate 21 on which the organic light-receiving element unit 20 is attached are separated by the light-blocking member 29 surrounding the projection optical path 10, light can be prevented from being transmitted from the light source 40 via the transparent substrates.

In the foregoing, the present invention has been described in detail based on the embodiments thereof, but the present invention is not limited to the above-described embodiments. For example, materials of the transparent substrate 21, the transparent electrode 22, the organic photoelectric-conversion layer 23, the upper electrode 24, the upper circuit board 25, and the conductive film 42 are not limited to those described above, and may be changed to other materials having the same functions.

In the above-described embodiments, a configuration has been described in which the transparent electrode 22, the organic photoelectric-conversion layer 23, and the upper electrode 24 are stacked abutting one another in the organic light-receiving element unit 20. However, between the transparent electrode 22 and the organic photoelectric-conversion layer 23 and between the organic photoelectric-conversion layer 23 and the upper electrode 24, buffer layers may be included that will improve characteristics of the organic light-receiving element unit 20.

What is claimed is:
1. A probe for bioinstrumentation comprising:
a transparent substrate having flexibility;
an organic light-receiving element that is provided on the transparent substrate, includes an organic photoelectric-conversion layer sandwiched between a transparent electrode and an upper electrode, and, when light for measurement is radiated onto a subject, detects scattered light that is scattered by the subject;
an upper circuit board that has flexibility and is provided on the side opposite to the transparent substrate with respect to the organic light-receiving element, and is provided with wires therein that are connected with the transparent electrode and the upper electrode;
a projection optical path that is provided apart from the organic light-receiving element and transmits light for measurement along a thickness direction of the transparent substrate, the projection optical path formed as a through hole that penetrates from an upper side of the upper circuit board to a lower side of the transparent substrate; and
a connector that is attached to the upper circuit board and allows the wires to be externally connected, wherein
the upper electrode has a light-blocking effect and covers an end of the organic photoelectric-conversion layer on the side of the projection optical path.

2. The probe for bioinstrumentation according to claim 1, further comprising a light-blocking member that is provided, to block light from the projection optical path, between the projection optical path and the organic light-receiving element.

3. The probe for bioinstrumentation according to claim 1, wherein
- a light source is provided, to emit the light for measurement, on the upper circuit board at the upper end of the through hole.

4. The probe for bioinstrumentation according to claim 1, wherein
- an organic light-emitting diode (LED) is provided, to emit the light for measurement, on the transparent substrate apart from the organic light-receiving element, and
- the projection optical path is formed in the transparent substrate under the organic LED.

5. The probe for bioinstrumentation according to claim 1, wherein
- the organic light-receiving element is formed in a ring-shaped manner, and
- the projection optical path is provided in a central portion inside the organic light-receiving element.

6. A bioinstrumentation device comprising:
- the probe for bioinstrumentation according to claim 1;
- a cable that is connected with a connector of the probe for bioinstrumentation; and
- a measurement unit that is connected with the probe for bioinstrumentation through the cable and acquires information on the inside of the subject based on a detection signal from the organic light-receiving element of the probe for bioinstrumentation.

* * * * *